United States Patent
Andreff et al.

(10) Patent No.: US 11,048,331 B2
(45) Date of Patent: Jun. 29, 2021

(54) HAPTIC FEEDBACK DEVICE

(71) Applicants: Centre National de la Recherche Scientifique, Paris (FR); UNIVERSITE DE FRANCHE-COMTE, Besancon (FR)

(72) Inventors: Nicolas Andreff, Ecole-Valentin (FR); Marc Viallon, Morteau (FR); Sergio Lescano, Besancon (FR)

(73) Assignees: Centre National de la Recherche Scientifique, Paris (FR); UNIVERSITE DE FRANCHE-COMTE, Besancon (FR)

( * ) Notice: Subject to any disclaimer, the term of this patent is extended or adjusted under 35 U.S.C. 154(b) by 0 days.

(21) Appl. No.: 16/762,430

(22) PCT Filed: Nov. 8, 2018

(86) PCT No.: PCT/EP2018/080541
§ 371 (c)(1),
(2) Date: May 7, 2020

(87) PCT Pub. No.: WO2019/092063
PCT Pub. Date: May 16, 2019

(65) Prior Publication Data
US 2020/0356174 A1    Nov. 12, 2020

(30) Foreign Application Priority Data
Nov. 8, 2017   (FR) ...................................... 1760477

(51) Int. Cl.
*G06F 3/0354* (2013.01)
*G06F 3/01* (2006.01)

(52) U.S. Cl.
CPC .......... *G06F 3/016* (2013.01); *G06F 3/03545* (2013.01)

(58) Field of Classification Search
CPC ............................. G06F 3/016; G06F 3/03545
See application file for complete search history.

(56) References Cited

U.S. PATENT DOCUMENTS

| 6,697,043 B1 * | 2/2004 | Shahoian ................ A63F 13/06 |
| | | 345/156 |
| 7,265,750 B2 | 9/2007 | Rosenberg |
| | | (Continued) |

FOREIGN PATENT DOCUMENTS

FR    2927709 A1    8/2009

OTHER PUBLICATIONS

Heller, M. A.. et al.; "Touch and Blindness Psychology and Neuroscience"; LEA Lawrence Erlbaum Associates, Publishers, 2006, (240 pages).

(Continued)

*Primary Examiner* — Gene W Lee
(74) *Attorney, Agent, or Firm* — Osha Bergman Watanabe & Burton LLP

(57) ABSTRACT

The invention relates to a haptic feedback device comprising:
a body (10) able to form an interface with a user;
contacting means (20) able to establish a contact with a surface (2) of a system (3) able to contain information;
a first actuator (30) linked to the contacting means and able to apply a translational movement to said contacting means with respect to said body;
braking means (40) able to apply a mechanical resistance to the relative movement between the contacting means (20) and the body (10);
a second actuator (50) able to make the mechanical resistance applied by the braking means (40) vary.

20 Claims, 5 Drawing Sheets

(56) References Cited

U.S. PATENT DOCUMENTS

| | | |
|---|---|---|
| 9,639,181 B2* | 5/2017 | Song .................... G06F 3/016 |
| 2015/0212578 A1 | 7/2015 | Lor et al. |
| 2016/0188015 A1* | 6/2016 | Song .................. G06F 3/0383 |
| | | 345/179 |
| 2017/0269691 A1 | 9/2017 | Fleureau et al. |
| 2019/0101994 A1* | 4/2019 | Kira .................... G06F 3/0383 |

OTHER PUBLICATIONS

Brooks, T.L.; "Telerobotic Response Requirements"; IEEE, 1990, pp. 113-120 (8 pages).
Dictionnaire sensagent (http://dictionnaire.sensagent.leparisien.fr/haptique/fr-fr/) Sep. 3, 2020 (23 pages).
International Search Report issued in Application No. PCT/EP2018/080541, dated Jan. 25, 2019 (6 pages).
Written Opinion issued in International Application No. PCT/EP2018/080541, dated Jan. 25, 2019 (8 pages).

\* cited by examiner

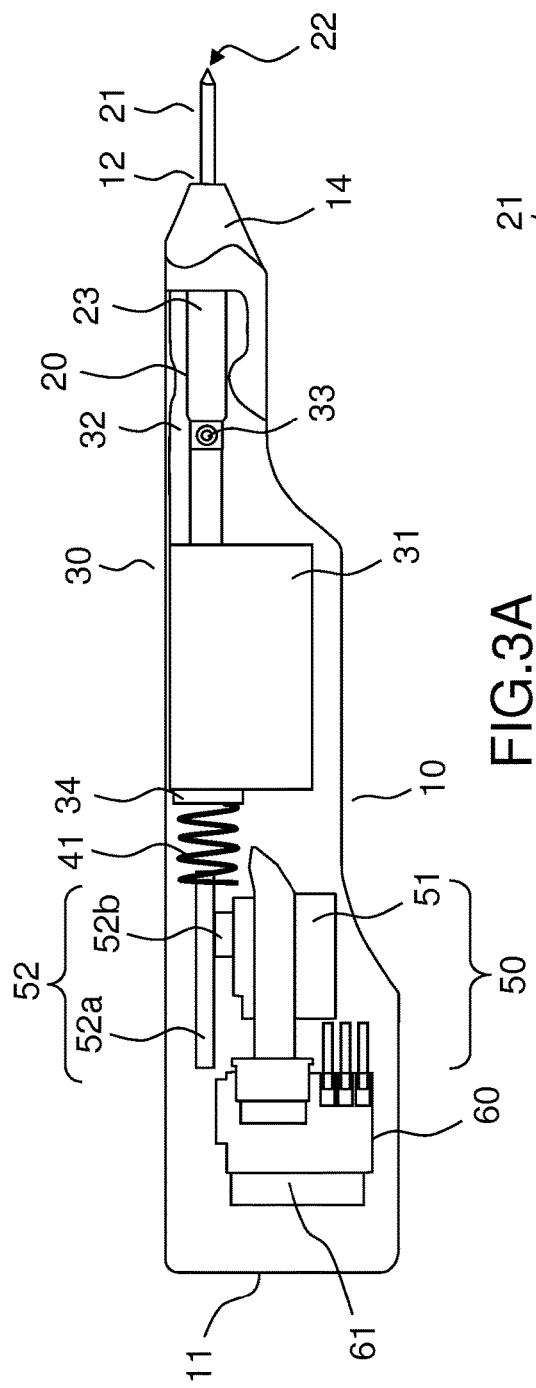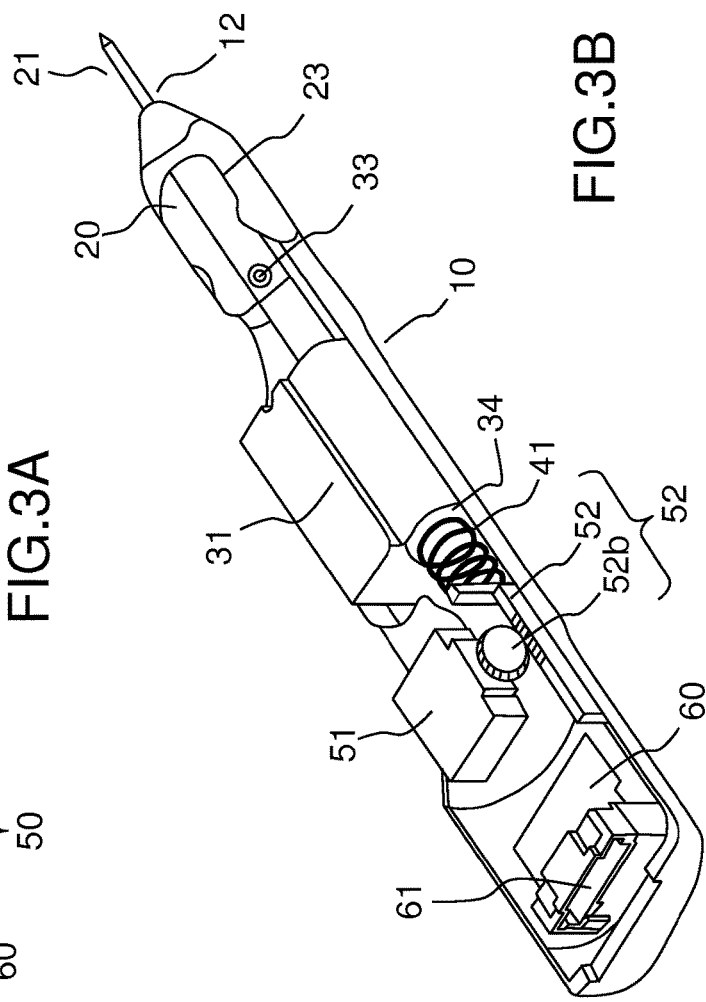
FIG.3A
FIG.3B

HAPTIC FEEDBACK DEVICE

TECHNICAL FIELD

The invention relates to a haptic feedback device, i.e. to a device able to transmit, to a user, (remote) feedback in terms of vibrations, movements, temperature changes, etc. allowing him to feel a texture, a shape, a force, heat, etc. The invention particularly relates to a haptic feedback device allowing feedback to be transmitted as to the relief and stiffness of an environment or of an object.

The invention is applicable to the fields of:

robot-assisted surgery, in which field it is necessary to achieve the highest possible precision, particularly in the field of assisted microsurgery;

medical imaging, which in particular allows information to be collected, measured and stored in a computer system, which information may be remotely retrieved by a user;

computer aided design, in particular for the design and manufacture of furniture, to get a feel of shapes, comfort, etc.

teleoperation, in particular in nuclear fields in which operations are carried out remotely;

activities supporting reeducation;

assistance of the visually impaired;

games, in particular video games, etc.

and more generally in any case in which it is desired to create an indirect active hardware interface between the hand of a user and a real, augmented-reality or virtual environment or an object.

BACKGROUND

The invention more particularly relates to cases in which it is desired to create a hardware (or physical) interface between the hand of a user and a surface connected with a system able to contain information, for example information on an environment, on an inanimate or animate object (plants, animals, (magnetic, electric, etc.) fields for example). The surface may be a screen and the system a tablet computer, a smartphone, a desktop computer or equivalents thereof. The information may be converted into digital data.

The screen is preferably a touch screen. It is also referred to an activatable surface hereafter. In this case, an active layer is placed on the screen. This active layer comprises a sensitive surface that may be activated by the finger or hand of a user, or any other actuating means able to excite this active layer (electrically conductive means, mechanical means employing triangulation, etc.). Such an interface may also feed back information to the user, for example feed back information on the environment or the object, etc.

The sensitivity of the human sense of touch is the result of a complex mechanism in which a plurality of modalities are involved. In the context of the present invention, haptic systems, which allow information on an environment or an object to be delivered to the user via physiological feedback on this environment or this object, are of interest. When it is a question of force feedback, haptic systems call upon the physical, or kinesthetic, sense of touch, i.e. the sense associated with the nervous and muscular system of the operator. When it is a question of a surface finish, of a texture, or of a relief, haptic systems employ the sensorial receptors located at the end of the nerve endings of the skin, which are called Pacinian receptors.

As for example indicated in the publications:

"Telerobotics response requirements (IEEE international conference on systems Man and Cybernetics Brooks 1990)";

"Psychology of Touch and Blindness (Morton A. Heller, Edouard Gentaz 2013)";

"Dictionnaire sensagent (http://dictionnaire.sensagent.leparisien.fr/haptique/fr-fr/)", human beings are capable of feeling vibrations below a refresh frequency of about 10 kHz, and a variation in force (for example in the stiffness of a touched material) between about 30 and 300 Hz. In contrast, the perception of movement (for example to sense a relief, texture, or more generally a surface finish) is slower: 1 Hz if the movement is unexpected, 10 Hz for reflexes.

In other words, the sensitivity of human beings to force feedback is rapid, i.e. of a few milliseconds, and it is not necessary to transmit information of high amplitude to the user. To meet this physical constraint, it is therefore necessary to provide a system that reacts very rapidly (a few milliseconds), but that does not necessarily deliver a substantial movement, or that delivers information other than a movement. In contrast, the sensitivity of human beings to changes in shape (and therefore relief) is relatively slow (a few tenths of a second), especially if the variations are large; hence it is necessary to transmit information of "high" amplitude to the user. To meet this physical constraint, it is therefore necessary to provide a system that is able to deliver a "large" movement relative to the hand of a user (i.e. a few millimeters), but that does not necessarily react very rapidly (a few tenths of a second).

It is therefore not obvious how to meet the dual (and in addition contradictory) constraint that a designer is confronted with when it is desired to provide feedback on relief (or shape) and on force (or stiffness), and when it is therefore desired to provide, via the same device, feedback on very different or even contradictory information, above all if the device must not be too bulky.

For example, in the field of assisted microsurgery, and more particularly laser microsurgery of the vocal cords (or phono-surgery), the objective is to guide a laser beam in a precise way toward the vocal cords. So-called phono-surgery is defined as follows: "any surgical procedures that maintain, restore or improve the human voice", or even "the science of manipulating the vibratory elements of the larynx in order to restore vocal function". This implies excision of tissular masses that could be benign masses or cancerous lesions. In laser surgery, the use of a scalpel is replaced by the use of laser technologies. There are a variety of laser technologies.

The conventional methodology, which is widespread, for controlling the surgical laser remotely is a mechanical manipulator, with a surgical microscope positioned so as to view the vocal cords to be treated. This mechanical manipulator and the laser source may be located at about 400 mm from the vocal cords.

More recently, teleoperated surgical systems have been developed that are based on a microrobot that is employed as the terminal system of an adjustable flexible endoscope (or flexible laryngoscope in the case of vocal cords) for inserting the microrobot and cameras into the body of the patient, removing the need for the surgical microscope, and allowing regions that are inaccessible by the preceding technique to be accessed. These new laser-microsurgery systems provide a better accessibility and a better precision than the preceding systems.

A "surgeon-microrobot" interface in general delivers, to the surgeon, visual feedback via a tablet computer, in the form of images and/or photographs. The surgeon may also interact by means of the tablet computer and of a stylus, to mark the paths of the laser over the vocal cords, as may be seen in FIGS. 1A and 1B.

The problem with this interface is that the surgeon is unable to perceive the texture of the human tissue, unlike when he operates directly on said tissue. This lack of perception concerns both relief, which may for example provide information on the 3D shape of the tissue (replacing sight), and stiffness, which may for example provide information on the type of tissue and organ (replacing the sense of touch and the act of touching).

The objective of the invention is therefore not only to view and mark remotely the paths that the terminal system of the endoscope will have to follow, but also to feel the texture of the images remotely. The expression "feel the texture of the images" must be understood to mean that the user must be able to feel the stiffness of the tissues, but also their reliefs, for example the bumps and cavities of the tissues, and therefore also the stiffness of these reliefs, and all this via a single device such as a stylus.

This problem affects any user desiring to feel remotely an environment or an object in which or on which he is operating.

To meet this need, devices are already known that allow a user to receive feedback on a texture (or a surface finish), using a haptic device comprising a vibrating device for transmitting information to a user, such as for example in patent application US2015212578, which discloses a touch implement, a stylus for example, comprising a haptic device coupled to at least one controller and a sensor, coupled to the controller, that detects when the touch implement makes contact with a surface. The controller delivers haptic feedback via the haptic device in order to simulate a texture of the surface when the touch implement makes contact with the surface. Furthermore, the implement comprises a vibration device and the controller causes the vibration device to vibrate stronger to simulate a rougher texture and weaker to simulate a smoother texture.

The vibrators may comprise "linear voice coil" actuators in which a coil slides about a magnet to transmit a vibration to a touch surface of the device, such as for example in U.S. Pat. No. 7,265,750.

Alternatively, the actuators may comprise an armature that slides between two coils, the AC power supply of the coils allowing the armature to be attracted toward one or the other of the coils, thus creating an oscillating effect able to generate a vibration. The actuator is linked to a part in order to generate haptic feedback in a region of movement of the finger of a user, as in patent FR2927709.

None of these devices allows feedback to be received both on relief (or texture) and stiffness.

Virtual-reality devices allowing 3D vision do exist, but these devices are generally bulky, and they are not suitable for the targeted applications, and in particular for a surgeon, especially seeing as it would be necessary to complete them with a haptic force-feedback device. It would therefore be necessary to use two different devices, this being especially disadvantageous for a user required to make precise gestures.

The objective of the invention is to address the drawbacks of the haptic feedback devices of the prior art.

One objective is to provide a haptic feedback device that allows feedback to be obtained both on the relief and stiffness of an object or a real, virtual or augmented-reality environment that is light, transportable, not very bulky, and compatible with display surfaces such as touch screens.

SUMMARY OF THE INVENTION

To solve the aforementioned problem, the subject of the invention is a haptic feedback device comprising:
a body able to form an interface with a user;
contacting means able to establish a contact with a surface of a system able to contain information;
a first actuator linked to the contacting means and able to apply a translational movement to said contacting means with respect to said body;
braking means able to apply a mechanical resistance to the relative movement between the contacting means and the body;
a second actuator able to make the mechanical resistance applied by the braking means vary.

By longitudinal direction, what is meant is the direction of translation between the body of the device and the contacting means.

The surface of the system is preferably an activatable surface.

According to one embodiment, the device has substantially the form of a stylus. This form has the advantage of being ergonomic, light and easy to handle.

According to one embodiment, the body has at least one conductive portion.

According to one embodiment, the body is able to contain all or some of the first actuator and/or of the braking means and/or of the second actuator.

According to one embodiment, the body comprises a casing able to contain the first actuator, the second actuator, and the braking means.

According to one embodiment, the contacting means comprise a tip with a first end able to establish a contact with a surface. A tip furthermore allows the point touched on the surface to be more precise.

According to one embodiment, the first end of the tip is able to excite the surface.

According to one embodiment, the first actuator comprises a linear motor.

According to one embodiment, the device comprises first linking means able to link the first actuator to the contacting means.

According to one embodiment, the device comprises second linking means able to link the second actuator to the braking means.

According to one embodiment, the braking means comprise a spring. A spring is easy to implement, easy to make modular and the stiffness of the spring may easily be varied by adjusting the length of the spring.

According to one particular embodiment, the second actuator is able to make the stiffness of the spring vary by making the length of said spring vary.

According to one particular embodiment, the second actuator comprises a rotary motor.

According to one particular embodiment, the linking means comprise a link of rack-and-pinion type.

According to one embodiment, the device furthermore comprises powering means able to electrically connect the first and second actuators of said device.

According to one embodiment, the powering means comprise a battery.

According to one embodiment, the powering means (60) comprise an interface for plugging into an exterior power supply.

According to one embodiment, the powering means are able to electrically activate the contacting means.

According to one embodiment, the device furthermore comprises processing means able to activate the first actuator and the second actuator depending on the position of the contacting means on the surface.

BRIEF DESCRIPTION OF THE FIGURES

Other features and advantages of the invention will become apparent from the following non-limiting description, which is given, by way of illustration, with reference to the appended figures, in which:

FIGS. 3A and 3B illustrate a cross-sectional view and a 3D view of a device according to the same embodiment, with more details;

DETAILED DESCRIPTION OF PARTICULAR EMBODIMENTS

Figure 1A:
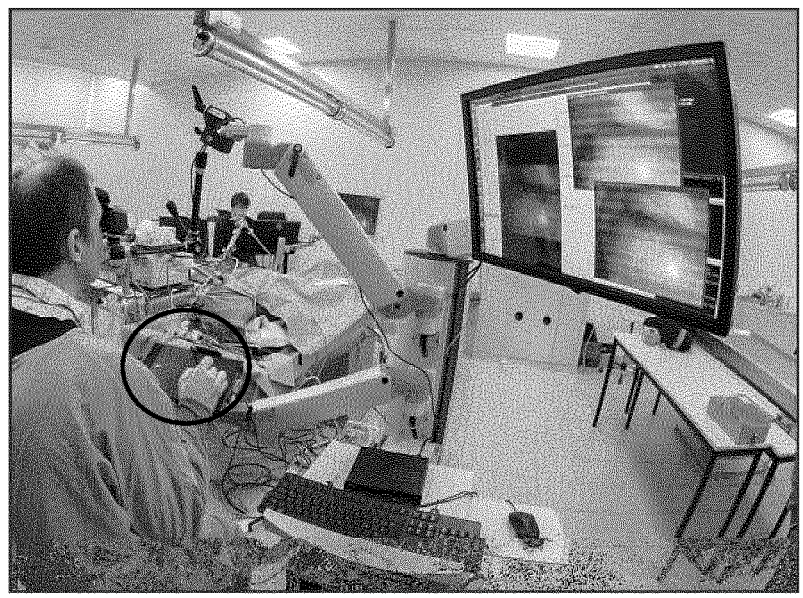
FIGS. 1A and 1B illustrate a working interface between a surgeon and a microrobot comprising a tablet computer and a stylus according to the prior art.
Figure 1B:
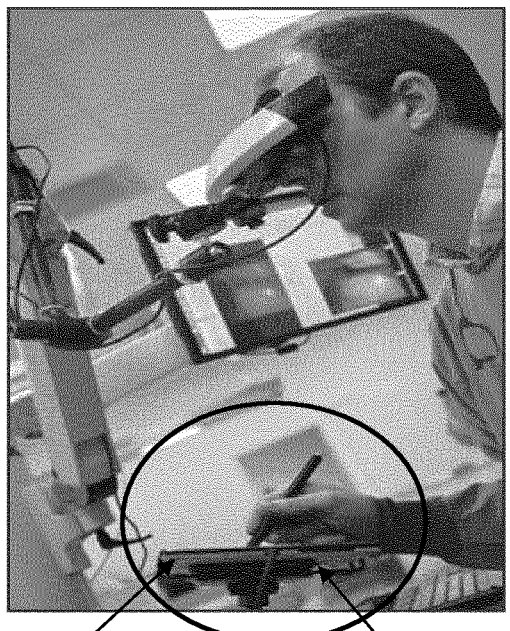

FIG. 1 has already been described and will not be referred to again here.

FIGS. 2, 3A, 3B, 4 and 5 illustrate the same embodiment, certain figures giving more details (mechanical details or electronic details or details of operation).

Figure 2:
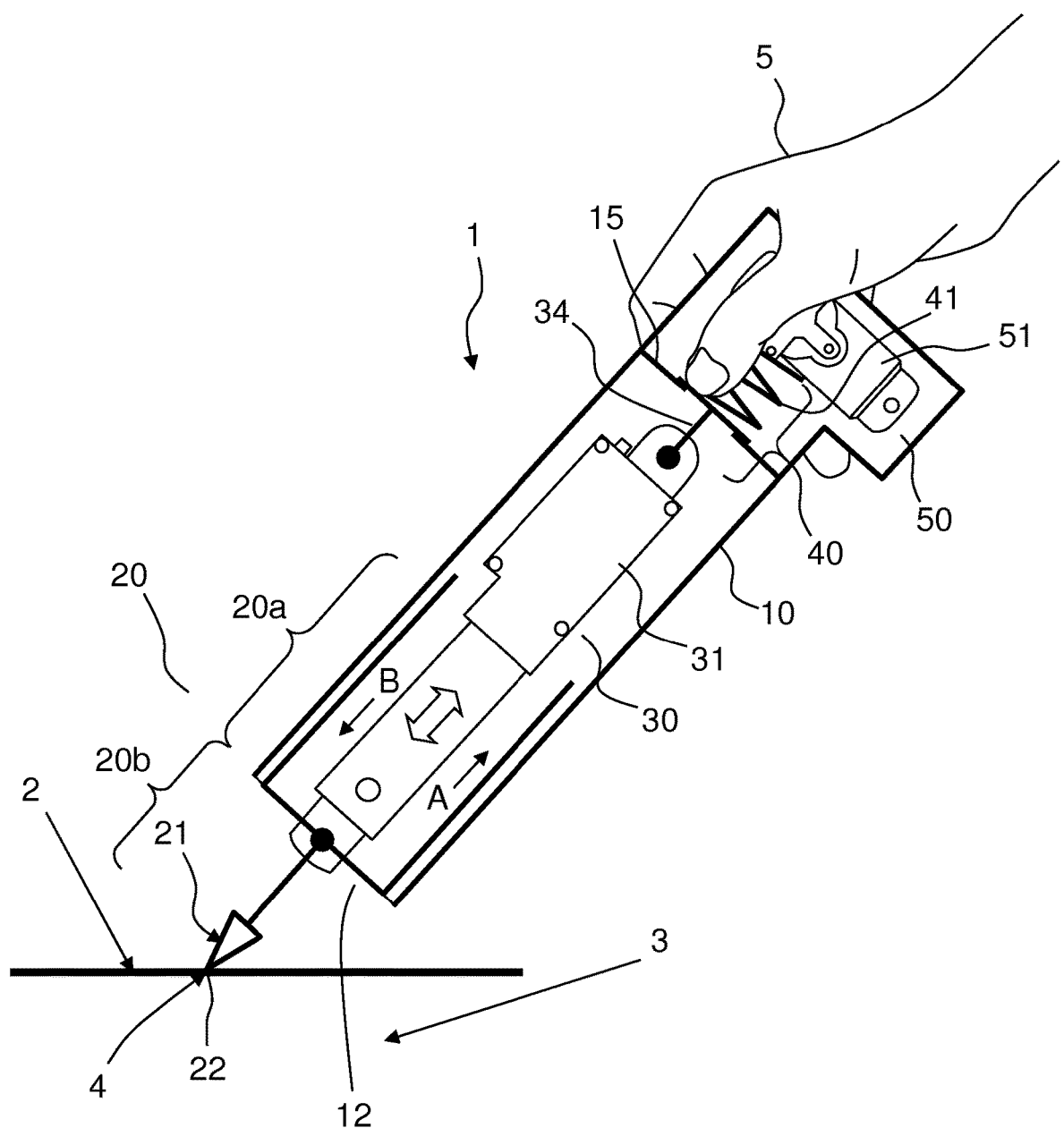
FIG. 2 shows a diagram of the device according to one embodiment.

FIG. 2 shows a diagram of the device according to the invention.

The haptic feedback device 1 comprises a body 10. A first end 11 of the body may be held in the hand 5 of the user, thus ensuring the interface with the latter. The first end 11 of the body may have an ergonomic shape able to promote a good grip and/or a good transmission of the movements to the hand of the user.

The device also comprises contacting means 20 having a tip 21.

When the tip is placed on an activatable surface such as a touch surface 2 of a system 3 able to contain data (a tablet computer, a smartphone, a desktop computer, etc.), it is necessary to provide a mode of excitation of said surface. For example, the excitation may be capacitive, inductive, mechanical or thermal.

The tip 21 may therefore be able to excite the activatable surface. For example, as illustrated, it may comprise a portion 22 able to excite said activatable surface. Thus, the tip 21, via the portion 22, allows a connection to be established in order to excite the activatable surface.

In the example shown, the excitation is electrical and the tip 21 comprises an electrically conductive portion 22. Alternatively, the tip 21 may be entirely conductive.

Figure 4:
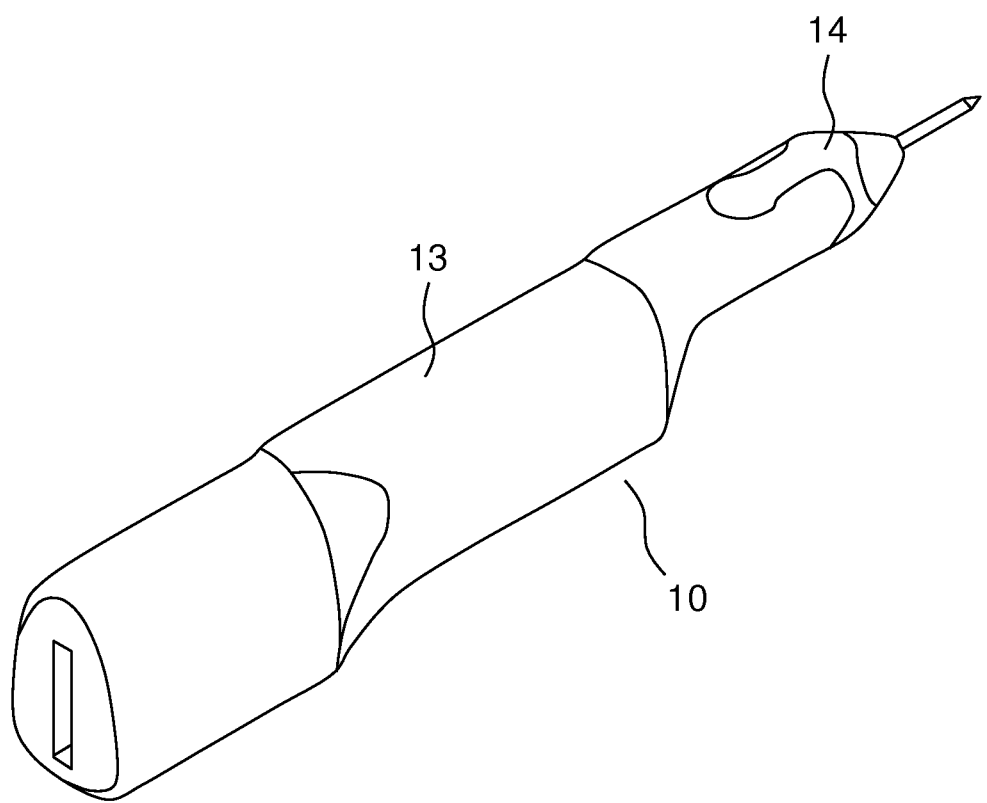
FIG. 4 shows an outside view of the same embodiment of the device.

Alternatively or in addition, the body 10 may comprise a conductive portion 14, which is shown in FIGS. 3A to 3B and 4. Said conductive portion of the body 10 is provided to facilitate the excitation of the activatable surface via the very existence of an, admittedly minimal, electrical voltage of the human body (of the user)

Specifically, the electrical excitation requires an electrical continuity to be able to communicate with the system 3. Commercially available tips 21 commonly use the electrical voltage of the human body, which is transmitted by the hand 5, and the electrical contact between the tip 21 and the hand 5 (moreover, the hand is sufficient to establish the continuity).

Alternatively, the tip 21 may be connected to an electrical system. This electrical connection may be achieved via powering means 60 that are described with reference to FIGS. 3A and 3B, a battery 62 (shown in FIG. 5) for example.

However, as there are other means for exciting an activatable surface, the tip 21 is not necessarily conductive. It may for example be made of plastic, and able to hold a charge on the surface 2 so as to excite said activatable surface.

Figure 5:
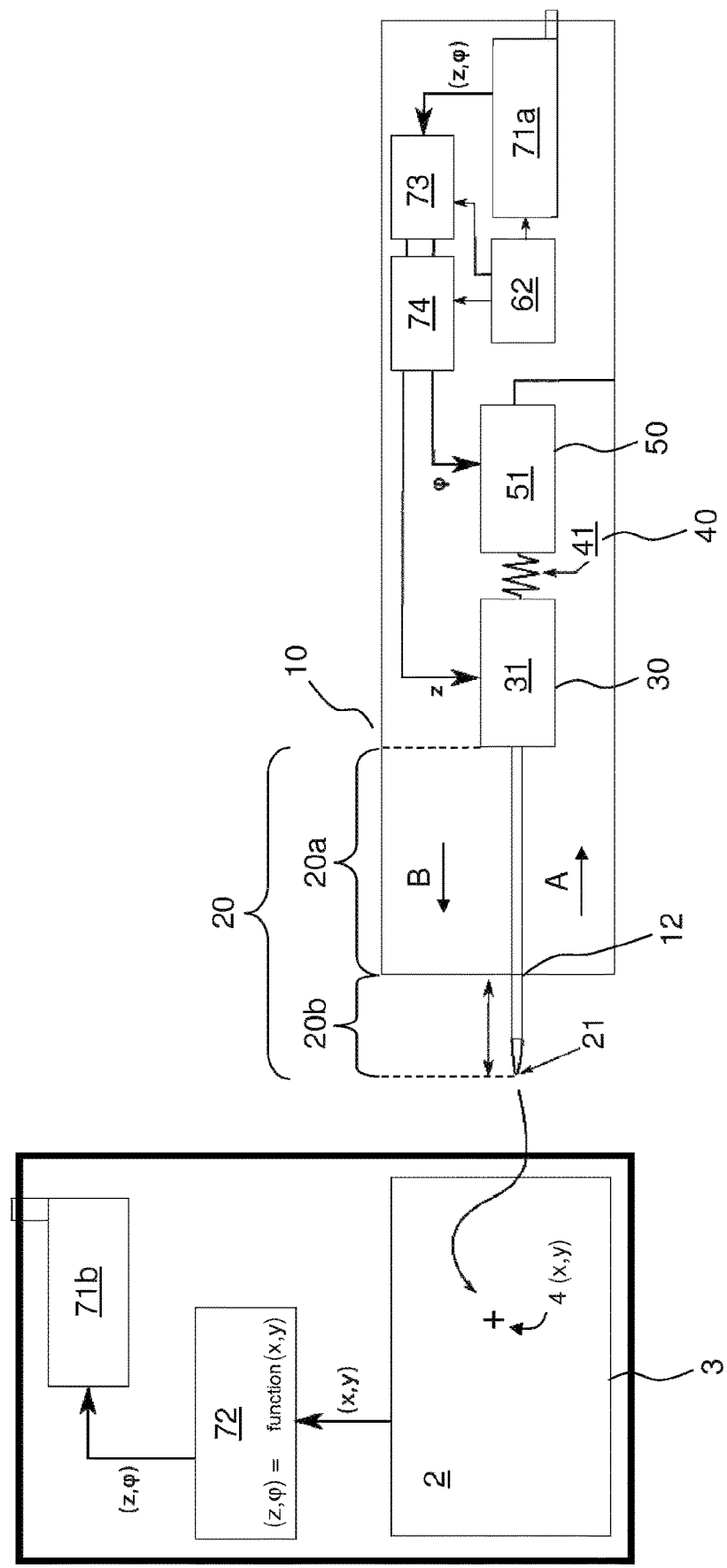
FIG. 5 illustrates and gives more details on the operation of a device according to the same embodiment.

As also illustrated in FIG. 5, when the tip 21 touches the activatable surface 2 of a system 3 able to contain data, such as a tablet computer, a smartphone or a desktop computer, it allows information to be received and transmitted between said system and the haptic feedback device 1.

For example, the tip 21 allows the x,y position of the point of contact 4 to be transmitted to the system 3, the system 3 delivering in return information on said point of contact (information on the relief, such as a thickness, a height and/or any other information allowing the relief to be characterized, and information on stiffness).

The information on relief is transmitted to the first actuator 30 so that it can react by applying, to the contacting means 20, via the tip 21 making contact with the surface 2 in the illustrated example, a translational movement with respect to the body 10. The amplitude and the direction of this translational movement depend on the information on relief transmitted by the system 3, which information is converted into a z value and/or into another value. Since the tip 21 remains in contact with the surface 2, it is the body 10 that will move by said z value:

either by pushing against the hand (direction A), for example to simulate a bump, a convexity, etc.

or by pulling out of the hand (direction B), for example in order to simulate a recess, a concavity, etc.

As shown in FIGS. 2 and 5, the contacting means 20 are configured to make reciprocal translational movements with respect to the body 10, a first portion 20a of said contacting means being able to slide essentially inside said body and a second portion 20b being able to slide inside and outside said body. The second portion 20b comprises the tip 21. The body 10 has an aperture 12 able to allow the passage of the contacting means 20 between inside and outside said body 10.

As illustrated, the first actuator 30 comprises a linear first motor 31. Said first motor 31 is linked to the contacting means 20 and it allows a translational movement to be applied to said contacting means 20 with respect to the body 10. A linear motor has the advantage of being easy to adapt to the elongate shape of the device, this in particular facilitating assembly thereof.

Alternatively, the first motor 31 may operate rotationally, and be associated with mechanical means (ball screw, transmission system) allowing the rotational movement to be converted into a translational movement. The advantage of a rotary motor is that it is in general less bulky.

The information on stiffness is transmitted to the second actuator 50 so that it may act on the braking means 40 so as to make said second actuator vary the mechanical resistance applied by said braking means 40 to the movements between the contacting means 20 and the body 10 of the device. This mechanical resistance is therefore felt by the hand 5 of the user in contact with the body 10. This mechanical resistance felt by the user depends on the information on stiffness transmitted by the system 3, which information is converted into a φ value and/or into another value.

As illustrated, the braking means 40 comprise a spring 41 that allows a variable mechanical resistance depending on the stiffness of said spring to be applied. The second actuator 50 comprises a second motor 51 linked to said spring and that acts to increase or decrease the length of said spring. On doing this, it decreases or increases the stiffness of said spring. This stiffness is applied to the movement between the tip 21 and the body 10 of the device, when the tip 21 is in contact with the surface 2.

As illustrated, the second motor 51 operates rotationally and may therefore rotate by the angle φ. A rotary motor allows bulk to be decreased. Furthermore, it allows a better precision to be obtained.

Alternatively, the second motor may operate translationally, or with any other movement allowing the length, and therefore the stiffness, of the spring to be modified.

As illustrated, the first actuator 30 and the braking means 40 coupled to the second actuator 50 are placed in series. The first motor 31 is linked to the spring 41 by first linking means 34 that comprise a T-shaped rod, the longitudinal portion of the T being coupled to the first motor 31 and the transverse portion of the T being coupled to the spring 41. The transverse portion of the T is retained by a rigid ring 15 that is fastened transversely to the inside of the body 10, so that the length of the spring cannot exceed a certain length. In other words, the rigid ring 15 allows a reference to be defined for the base of the spring with respect to the body 10.

This series configuration allows bulk to be limited in the transverse direction of the haptic feedback device. It allows the body 10 to have an elongate shape, as is required when the body 10 has a stylus shape, as illustrated in the following figures.

Alternatively, the first actuator 30 and the braking means 40 coupled to the second actuator 50 may be arranged in parallel.

FIGS. 3A and 3B illustrate a cross-sectional view and a 3D view of the same embodiment, with more details. FIG. 4 illustrates the same embodiment seen from outside.

The body 10 comprises a casing 13, which may be seen in FIG. 4. The casing 13 may be made of a material able to withstand the weight of the components that it contains, for example a strong plastic. Said casing contains the first and second actuators 30, 50 and the braking means 40.

The body 10 has an aperture 12 so that the contacting means 20 can pass through said body.

The body 10 may also comprise an end fitting 14. The aperture 12 may be produced in said end fitting. The body may therefore not be monolithic: for example, the end fitting 14 may be made of a conductor and the rest of the body 10 may be made of an insulator. The end fitting 14 may be connected to the casing 13, for example by clip fastening or interlocking or via a threading system.

The contacting means 20 are partially contained in the body 10 and comprise a tip 21 linked to a rod 23. The tip 21 has a diameter smaller than the rod 23. The aperture 12 of the body 10 has a diameter larger than the diameter of the tip 21 but smaller than the diameter of the rod 23, so that only said tip can enter and exit said body.

The illustrated device takes the form of a stylus.

The first actuator 30 comprises a linear first motor 31, as described with reference to FIG. 2. The first actuator 30 is linked to the contacting means 20 via a link 32 of pivot type, said link 32 being maintained by a pin 33.

The braking means 40 comprise a spring 41, as described with reference to FIG. 2.

The second actuator 50 comprises a rotary second motor 51, as described with reference to FIG. 2.

The movement of the device 1 is achieved via the contacting means 20 and more precisely the tip 21 of said contacting means (which is therefore also the tip of the stylus). Said tip is actuated by the first motor 31, but also by the spring 41 the stiffness of which is adjusted by the motor 51. The motor 31 and the spring 41 coupled to the motor 51 are mounted in series one after the other. The first motor 31 is linked to the spring 41 by the linking means 34, which were described above.

The first motor 31, which may be designated a "linear actuator", serves to transmit the relief information, and the rotary second motor 51, which may be designated a "servomotor", is coupled to the spring 41, which serves to transmit the stiffness information. The harder the actual surface corresponding to the point of contact 4, the more the spring will be compressed by the servomotor, and the higher the mechanical resistance of the tip 21 against the surface 2 making contact with the stylus will then be. Conversely, the softer the actual surface corresponding to the point of contact 4, the less the spring will be compressed by the servomotor, and the lower the mechanical resistance of the tip 21 against the surface 2 making contact with the stylus will then be.

In the illustrated example, the transmission of the rotational movement output from the servomotor 51 to the spring 41 is achieved by second linking means 52, for example a link of rack-and-pinion type. The link 52 of rack-and-pinion type makes it possible to convert the rotational movement of the servomotor 51 into a translation applied to the spring 41. The pinion 52b is linked to the servomotor 51 and the rack 52a is linked to the spring 41 so that the latter is compressed or released under the action of said servomotor.

The stiffness of the spring is then taken into account by the linear actuator 31 that, for its part, moves the tip 21 with a translational movement with respect to the body 10. The translational movement applied to the tip 21 is associated with a mechanical resistance that increases or decreases, depending on the spring stiffness applied.

Since the tip 21 makes contact with the surface 2, it is the body of the stylus 1 that receives these movements and transmits them to the hand of the user making contact with the end 12 of the stylus.

Thus, the linear actuator 31 allows relief information corresponding to the point of contact 4 to be physically transmitted to a user, and the pair consisting of the servomotor 51 and the spring 41 allows stiffness information associated with said relief to be physically transmitted to a user.

With a device according to the invention, it is possible to feel reliefs of a few millimeters for a scanned area of a few square centimeters, this already being amply sufficient for certain users that must make careful and precise gestures.

The "scanned area" typically is the size of the image of an object seen on a screen. The image seen on the screen and that must be "felt" with the haptic device according to the invention may have a scale tailored to the application. For microsurgery, the image represents an "enlarged" object, in order to allow the objective to be better targeted. For example, on a screen of a touch-screen tablet computer of 20 cm×30 cm, it may be common to display the image of an object the actual size of which is for example 2 cm×3 cm.

Actuators and braking means of small sizes, i.e. of a few centimeters in size, may be used, and they may be configured with respect to one another so that the haptic feedback device may be the size of a stylus (of about 10 cm by 3 cm). By way of example:

the actuator 30 may be a Firgelli linear actuator (model: PQ12-100-6) the outside dimensions of which are 21.5 mm×15 mm×36.5 mm;

the braking means 40 may be a compression spring the dimensions of which are φ=9.4 mm and L=16 mm;

the actuator 50 may be an UltraNano servomotor from Hitec (model HS-35HD) the outside dimensions of which are 18.6 mm×15.5 mm×7.6 mm;

the power supply 60 is a 6 Vdc voltage source: it may be an external feed or a battery 62 placed inside the body 10 (illustrated in FIG. 5);

the boards 70 are standard boards intended for the control of the two motors and for the communication with the system 3.

The amplitudes of translation may also be dimensioned, for example by determining a tip length, by determining a stylus length and by modifying if necessary the first actuator and in particular its movement.

The applicable mechanical-resistance values may also be easily modifiable, for example by modifying the type of spring or by replacing a spring with another means.

Thus, the device according to the invention is very modular, and easily adjustable depending on the objects and the environment to be reproduced.

The device furthermore comprises powering means 60, which are able to electrically power the linear actuator 31 and the servomotor 51. As illustrated, the powering means may comprise a connection port 61 able to interact with a plug connected to a power supply outside the stylus.

FIG. 5 illustrates and gives more detail on the operation of a device according to the same embodiment.

As illustrated, the haptic feedback device according to the invention may comprise processing means 70.

Said processing means 70 may take the form of one or more circuit boards certain of which may be placed in the body 10 of the device, for example:

at least one communication board 71 able to establish a protocol for communication between the device 1 and the system 3, and in particular in order to exchange the information on the x, y coordinates of the point of contact 4, and the information (on relief or on stiffness) of said system for said point of contact: a first communication board 71a may be in the device 1 and a second communication board 71b may be in the system 3;

a computational board 72 for converting the information into values, for example into a z value for relief, and into a φ value for stiffness: it may be in the device 1 or in the system 3 (as shown);

a command/control board 73 able to control the first actuator 30 and the second actuator 50, for example in order to transmit, to the first actuator 30, a translational command depending on the z value and, to the second actuator 50, a rotational command depending on the φ value, in order to modify the resistance applied by the braking means 40, depending on the information transmitted by the system 3 for the point of contact 4: it may be in the device 1 (as shown);

a power board 74 so that these actions may be taken: it may be in the device 1 (as shown).

In the example shown, the power board 74 is powered by a battery 62.

Alternatively, it may be a question of communication means and/or computational means and/or command/control means and/or power means that are not necessarily boards, but that perform the same functions.

The haptic feedback device according to the example shown therefore operates as follows:

the tip 21 of the contacting means 20 makes contact at a point 4 with the activatable surface 2 of a system 3, so as to excite said surface and allow the system 3 to locate the x, y coordinates of the point of contact 4;

the system 3 returns information corresponding to the x,y coordinates of the point of contact 4: height, thickness and/or any other information allowing relief to be characterized and any information allowing stiffness to be characterized;

the returned information are converted into values (z for relief and φ for stiffness);

the z value is transmitted to the linear actuator (first motor 31) so that it may apply a translational movement z to the contacting means 20 with respect to the body 10;

the φ value is transmitted to the servomotor (second actuator 51) so that it may make a rotation φ in order to modify the mechanical resistance of the spring 41;

next, the user may move the haptic feedback device over the surface 2 and the process described above is reiterated.

The system 3 able to contain information may be a tablet computer and the surface 2 a touch screen of the tablet computer.

The present invention is not limited to the embodiment described above but encompasses any embodiment falling within the scope of the claims.

The invention may have many applications, in particular in the fields of:

robot-assisted surgery, in which field it is necessary to achieve the highest possible precision, particularly in the field of assisted microsurgery;

medical imaging, which in particular allows information to be stored in a computer system, which information may be browsed remotely by a user;

computer aided design, in particular for the design and manufacture of furniture, to get a feel of shapes, comfort, etc.

teleoperation, in particular in nuclear fields in which operations are carried out remotely;

activities supporting reeducation;

assistance of the visually impaired;

games, in particular video games, etc.

and more generally in any case in which it is desired to create an indirect active hardware interface between the hand of a user and a real, augmented-reality or virtual environment or an object.

The invention claimed is:

1. A haptic feedback device comprising:
    a body able to form an interface with a user;
    contacting means able to establish a contact with a surface of a system able to contain information;
    a first actuator linked to the contacting means and able to apply a translational movement to said contacting means with respect to said body;
    braking means able to apply a mechanical resistance to the relative movement between the contacting means and the body;
    a second actuator able to make the mechanical resistance applied by the braking means vary.

2. The device as claimed in claim 1, having substantially the form of a stylus.

3. The device as claimed in claim 1, the body having at least one conductive portion.

4. The device as claimed in claim 1, the body being able to contain all or some of the first actuator and/or of the braking means and/or of the second actuator.

5. The device as claimed in claim 1, the body comprising a casing able to contain the first actuator, the second actuator, and the braking means.

6. The device as claimed in claim 1, the contacting means comprising a tip with a first end able to establish a contact with a surface.

7. The device as claimed in claim 6, the first end of the tip being able to excite the surface.

8. The device as claimed in claim 1, the first actuator comprising a linear motor.

9. The device as claimed in claim 1, comprising first linking means able to link the first actuator to the contacting means.

10. The device as claimed in claim 1, comprising second linking means able to link the second actuator to the braking means.

11. The device as claimed in claim 1, the braking means comprising a spring.

12. The device as claimed in claim 11, the second actuator being able to make the stiffness of the spring vary by making the length of said spring vary.

13. The device as claimed in claim 1, the second actuator comprising a rotary motor.

14. The device as claimed in claim 13, the linking means comprising a link of rack-and-pinion type.

15. The device as claimed in claim 1, further comprising powering means able to electrically connect the first and second actuators of said device.

16. The device as claimed in claim 15, the powering means comprising a battery.

17. The device as claimed in claim 15, the powering means comprising an interface for plugging into an exterior power supply.

18. The device as claimed in claim 15, the powering means being able to electrically activate the contacting means.

19. The device as claimed in claim 1, further comprising processing means able to activate the first actuator and the second actuator depending on the position of the contacting means on the surface.

20. The device as claimed in claim 1, wherein the first actuator and the braking means coupled to the second actuator are placed in series.

* * * * *